United States Patent
Forrester (10) Patent No.: US 9,365,004 B2
(45) Date of Patent: *Jun. 14, 2016

(54) FLEXIBLE STRETCH HOSE HAVING INWARDLY EXTENDING WEB PORTIONS CONNECTING ADJACENT PAIRS OF REINFORCING COILS, WITH HOSE PROPERTIES ENHANCED BY ANNEALING

(71) Applicant: SCHAUENBURG HOSE TECHNOLOGY GMBH, Muelheim An der Rhu (DE)

(72) Inventor: Martin E Forrester, Trenton (CA)

(73) Assignee: Schauenburg Hose Technology GMBH, Muelheim An Der Rhu (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/987,837

(22) Filed: Sep. 6, 2013

(65) Prior Publication Data

US 2014/0130931 A1 May 15, 2014

Related U.S. Application Data (63) Continuation-in-part of application No. 13/986,465, filed on May 6, 2013, which is a continuation of application No. 12/799,263, filed on Apr. 21, 2010, now Pat. No. 8,453,681, which is a continuation-in-part of application No. 12/354,291, filed on Jan. 15, 2009, now abandoned.

(60) Provisional application No. 61/335,023, filed on Dec. 30, 2009.

(51) Int. Cl.
*B29D 23/18* (2006.01)
*B29D 23/00* (2006.01)
(Continued)

(52) U.S. Cl.
CPC .............. *B29D 23/00* (2013.01); *B29C 53/785* (2013.01); *F16L 11/115* (2013.01); *F16L 11/118* (2013.01); *A61M 16/08* (2013.01); *B29C 53/58* (2013.01);
(Continued)

(58) Field of Classification Search
CPC ......... A61M 16/08; F16L 11/00; F16L 11/04; F16L 11/08; F16L 11/10; F16L 11/11–11/115; B29C 53/58; B29C 53/582; B29C 2071/022; B29L 2023/18; B29D 23/18
USPC ................... 156/143, 144; 264/235, 346, 567
See application file for complete search history.

(56) References Cited

U.S. PATENT DOCUMENTS

| 2,430,081 A | 11/1947 | Thomas et al. ............... 156/144 |
| 2,739,616 A | 3/1956 | Duff .............................. 138/122 |

(Continued)

FOREIGN PATENT DOCUMENTS

| DE | 3312 434 A1 | 4/1983 |
| DE | 84 26 279 U1 | 9/1984 |

(Continued)

*Primary Examiner* — Carson Gross
(74) *Attorney, Agent, or Firm* — David A. Burge (57) ABSTRACT

A flexible, stretchable, crush resistant hose particularly well suited for supplying breathing gases to patients in medical applications and the like has a helix defined by reinforcing coils of thermoplastic material, and a web of thermoplastic material bonded or welded to adjacent ones of the coils, preferably near outer diameter portions of the coils. The web extends radially inwardly between the adjacent pairs of the reinforcing coils to define a helical reverse-direction crease that can be located closer to or farther from a centerline of the hose than is the inner diameter of the reinforcing coils. The thermoplastic material of the hose is stress relieved by an annealing process performed during axial compression of the hose at a time after the hose has been formed.

15 Claims, 6 Drawing Sheets

(51) Int. Cl.
*F16L 11/115* (2006.01)
*F16L 11/118* (2006.01)
B29C 53/78 (2006.01)
*F16L 11/11* (2006.01)
*F16L 11/04* (2006.01)
*B29C 71/02* (2006.01)
*B29L 23/18* (2006.01)
*F16L 11/112* (2006.01)
*B29C 53/58* (2006.01)
*A61M 16/08* (2006.01)
*F16L 11/08* (2006.01)

(52) U.S. Cl.
CPC ......... *B29C 53/582* (2013.01); *B29C 2071/022* (2013.01); *B29L 2023/18* (2013.01); *F16L 11/04* (2013.01); *F16L 11/08* (2013.01); *F16L 11/11* (2013.01); *F16L 11/111* (2013.01); *F16L 11/112* (2013.01)

(56) References Cited

U.S. PATENT DOCUMENTS

| | | | | |
|---|---|---|---|---|
| 2,740,427 A | 4/1956 | Swan | | 138/122 |
| 3,122,171 A | 2/1964 | Britton et al. | | 138/129 |
| 3,674,056 A | 7/1972 | D'Aprile | | 138/134 |
| 3,739,815 A | 6/1973 | Rejeski | | 138/122 |
| 3,858,615 A * | 1/1975 | Weigl | | 138/121 |
| 3,861,424 A | 1/1975 | Mizutani et al. | | 138/119 |
| 3,910,808 A | 10/1975 | Steward | | 156/429 |
| 3,962,019 A | 6/1976 | Rejeski | | 156/428 |
| 3,963,856 A | 6/1976 | Carlson et al. | | 174/47 |
| 3,966,525 A | 6/1976 | Steward | | 156/195 |
| 4,038,519 A | 7/1977 | Foucras | | 219/301 |
| 4,043,856 A | 8/1977 | Steward | | 156/195 |
| 4,098,298 A | 7/1978 | Vohrer | | 138/122 |
| 4,294,636 A | 10/1981 | Vitellaro | | 156/143 |
| 4,304,266 A | 12/1981 | Kutnyak et al. | | 138/129 |
| 4,337,800 A | 7/1982 | Carlson et al. | | 138/122 |
| 4,375,381 A | 3/1983 | Carlson et al. | | 156/195 |
| 4,383,555 A | 5/1983 | Finley | | 138/129 |
| 4,489,759 A | 12/1984 | Yamamura | | 138/122 |
| 4,587,145 A | 5/1986 | Kanao | | 428/36 |
| 4,599,784 A | 7/1986 | Canu, Jr. et al. | | 29/450 |
| 4,686,354 A | 8/1987 | Makin | | 219/301 |
| 4,714,508 A | 12/1987 | Chivens et al. | | 156/195 |
| 4,780,261 A | 10/1988 | Vajtay | | 264/285 |
| 4,826,423 A | 5/1989 | Kemp et al. | | 425/505 |
| 5,357,948 A | 10/1994 | Eilentropp | | 128/204.17 |
| 5,454,061 A | 9/1995 | Carlson | | 392/478 |
| 5,537,996 A | 7/1996 | McPhee | | 128/204.17 |
| 5,555,915 A | 9/1996 | Kanao | | 138/133 |
| 5,637,168 A * | 6/1997 | Carlson | | 156/143 |
| 5,848,223 A | 12/1998 | Carlson | | 392/478 |
| 6,024,132 A | 2/2000 | Fujimoto | | 138/122 |
| 6,152,186 A | 11/2000 | Arney et al. | | 138/129 |
| 6,190,480 B1 | 2/2001 | Carlson | | 156/143 |
| 6,219,490 B1 | 4/2001 | Gibertoni et al. | | 392/472 |
| 6,305,428 B1 | 10/2001 | Nakamura et al. | | 138/126 |
| 6,347,646 B2 | 2/2002 | Fukui et al. | | 138/129 |
| 6,394,143 B1 | 5/2002 | Diels et al. | | 138/121 |
| 6,659,136 B2 | 12/2003 | Fukui et al. | | 138/125 |
| 6,827,109 B2 | 12/2004 | McCaughtry | | 138/134 |
| 6,948,527 B2 | 9/2005 | Ragner et al. | | 138/119 |
| 7,156,127 B2 | 1/2007 | Moulton et al. | | 138/122 |
| 7,431,054 B2 | 10/2008 | Kramer, Jr. et al. | | 138/133 |
| 7,468,116 B2 | 12/2008 | Smith et al. | | 156/344 |
| 7,520,302 B2 | 4/2009 | Smith | | 138/118 |
| 7,597,119 B2 | 10/2009 | Boettner | | 138/119 |
| 8,544,504 B2 | 10/2013 | Castro | | 138/121 |
| 2003/0098084 A1 | 5/2003 | Ragner et al. | | 138/129 |
| 2006/0165829 A1 | 7/2006 | Smith et al. | | 425/113 |
| 2008/0035229 A1 | 2/2008 | Kramer et al. | | 138/132 |
| 2009/0050227 A1 | 2/2009 | Smith | | 138/122 |
| 2009/0078259 A1 | 3/2009 | Kooij et al. | | 128/205.25 |
| 2009/0277525 A1 | 11/2009 | Jourdan | | 138/122 |
| 2010/0215351 A1 | 8/2010 | Forrester et al. | | 392/481 |
| 2011/0247619 A1 | 10/2011 | Formica et al. | | 128/204.18 |
| 2014/0326395 A1 | 11/2014 | Forrester et al. | | 156/195 |
| 2014/0332108 A1 | 11/2014 | Forrester et al. | | 138/122 |

FOREIGN PATENT DOCUMENTS

| | | |
|---|---|---|
| DE | 38 35 248 A1 | 10/1988 |
| DE | 40 39 215 A1 | 12/1990 |
| DE | 295 07 806 U2 | 5/1995 |
| DE | 695 27 528 T2 | 5/1995 |
| DE | 197 52 008 A1 | 11/1997 |
| DE | 199 04 864 A1 | 2/1999 |
| DE | 20 2005 013 786 | 12/2005 |
| EP | 0097901 | 6/1983 |
| EP | 0201985 | 2/1986 |
| EP | 0742399 | 5/1996 |
| EP | 0917851 | 11/1997 |
| EP | 1181945 | 2/2002 |
| WO | WO 2004/011072 | 5/1995 |
| WO | WO 2006/094576 | 1/2006 |

\* cited by examiner

FLEXIBLE STRETCH HOSE HAVING INWARDLY EXTENDING WEB PORTIONS CONNECTING ADJACENT PAIRS OF REINFORCING COILS, WITH HOSE PROPERTIES ENHANCED BY ANNEALING

CROSS-REFERENCE TO RELATED PARENT APPLICATION

This application is a continuation-in-part of U.S. patent application Ser. No. 13/986,465 entitled METHOD OF HOSE MANUFACTURE, filed May 6, 2013 by Martin E. Forrester and Ralf Jourdan which was filed as a continuation of U.S. patent application Ser. No. 12/799,263 entitled FLEXIBLE, STRETCHABLE, CRUSH RESISTANT HOSE WELL SUITED FOR MEDICAL APPLICATIONS, filed Apr. 21, 2010 by Martin E. Forrester and Ralf Jourdan which not only claimed the benefit of the Dec. 30, 2009 filing date of provisional application Ser. No. 61/335,023 entitled FLEXIBLE HOSE FOR MEDICAL APPLICATIONS filed by Martin E. Forrester, but also was filed as a continuation-in-part of U.S. patent application Ser. No. 12/354,291 entitled STRETCH HOSE filed Jan. 15, 2009 by Ralf Jourdan.

The aforementioned continuation-in-part application Ser. No. 12/799,263 filed Apr. 21, 2010 issued on Jun. 4, 2013 as U.S. Pat. No. 8,453,681.

The disclosures of all of the documents that are referenced above are incorporated herein by reference.

FIELD OF THE PRESENT INVENTION

The present invention relates to the production of an improved form of extensible-retractable hose, commonly known as "stretch hose," formed from a combination of helically wound thermoplastic materials.

More specifically, the present invention relates to an improved form of stretch hose of a general type of stretch hoses that is disclosed and claimed in the aforementioned U.S. Pat. No. 8,453,681. Such stretch hoses as embody features of the present invention have adjacent pairs of reinforcing coils connected by a web of thermoplastic material that extends radially inwardly from where it joins with adjacent reinforcing coils near their maximum outer diameters—so that, when a hose retracts to its normal condition of minimal length, the web that connects each adjacent pair of reinforcing coils is sandwiched between the pair of adjacent reinforcing coils.

Introduction of Continuation-In-Part Application

This is a continuation-in-part application that relates both to an improved stretch hose, and to a method of forming an improved stretch hose that is flexible and easy-to-stretch, and is well suited for use in breathing circuitry, for example in providing a supply of air or anesthesia gas or gas-carried medication to a face mask such as is used with Continuous Positive Airway Pressure (CPAP) machines used to treat or assist in the prevention of sleep apnea.

The drawings of this continuation-in-part application include FIGS. 1-5 which also appear in parent U.S. application Ser. No. 12/799,263 and in U.S. Pat. No. 8,453,681. What is shown in FIGS. 1-5 does not show a hose embodiment that embodies radially inwardly extending web portions such as are claimed in the present continuation-in-part application.

The drawings hereof also include FIGS. 6-10 which do show a hose embodiment that utilizes radially inwardly extending web portions such as are a subject of the present continuation-in-part application.

Because this application is a continuation-in-part of an application which is a continuation of "parent application" Ser. No. 12/799,263, the description that immediately follows begins by including a reprint of the specification that appears in parent application Ser. No. 12/799,263, with no addition thereto of any substantive "new matter." Much of what is stated in the specification of application Ser. No. 12/799,263 is applicable to the invention of the present continuation-in-part application.

Specification of Parent application Ser. No. 12/799,263

The present invention relates to a flexible and easy-to-stretch hose that is crush resistant and well suited to provide a constant supply of air, anesthesia gas or gas-carried medication to a patient's face mask, nasal mask or tracheotomy tube for a variety of purposes such as anesthesia, life support or medication delivery, or to help prevent sleep apnea. Flexible, stretchable, crush resistant hoses embodying features of the invention are also well suited to evacuate gaseous pollutants from surgical areas, such as the removal of smoke during laser surgery.

Some prior crush resistant plastic hose proposals call for the use of solvents or glues to bond a web of thin material to coils of a helix that cooperate with the web to give the resulting hose its crush resistance. However, the use of solvents in the manufacture of crush resistant hoses is undesirable in medical applications because the resulting hoses may bring the patient into contact with trace amounts of the manufacturing solvent or glue, or the solvent or glue may react undesirably with medication being administered through the hose to a patient.

Some prior crush resistant plastic hose proposals intended for medical use are produced by extruding a thin web of plastic material to provide a connecting wall extending between adjacent coils of a helix of plastic. This connecting web may take a wavey form or may incorporate accordion-like folds that enable the hose to extend and contract in an accordion-like manner to give the resulting hose a measure of flexibility.

Although the hoses that result from the process just described may be effective in delivering air or gas-borne substances to the patient, the nature of the extrusion process used to produce these hose products typically causes the resulting hoses to exhibit a high degree of torsional stiffness and a diminished degree of flexibility due to the orientation of the molecules that form not only the thin wavy wall but also the helix that enhances the crush resistance of the hose. The torsional stiffness can cause a patient's face mask or nasal mask to lift off the face during movements of the patient's head, thereby allowing unwanted ambient air to enter the breathing circuit during therapy. The stiff nature of existing products also may cause undesirable stress on a tracheotomy tube during patient movement, and can render difficult head movements of a patient.

DESCRIPTION OF THE DRAWINGS

A fuller understanding of the invention may be had by referring to the following description, taken in conjunction with the accompanying drawings, wherein.

DETAILED DESCRIPTION FROM SER. NO. 12/799,263

Figure 1:
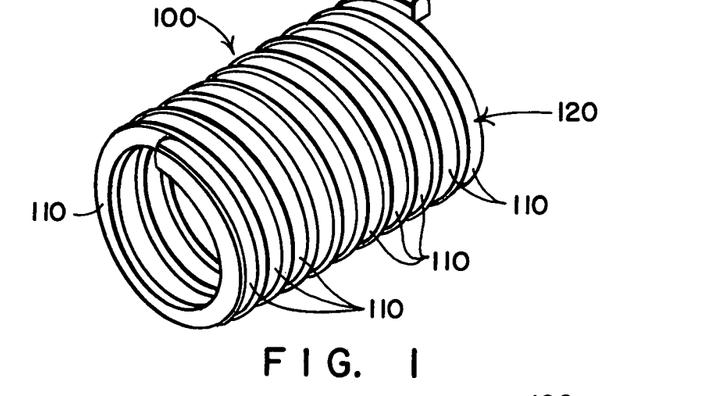
FIG. 1 is a perspective view showing a length of flexible, stretchable, crush resistant hose embodying features of the present invention, with the hose in its normally fully contracted condition wherein radially outwardly extending portions of a thin, extruded web of plastic material that extends between coils of a crush resistant plastic helix of the hose are snugly sandwiched between adjacent side-by-side coils of the helix.
Figure 2:
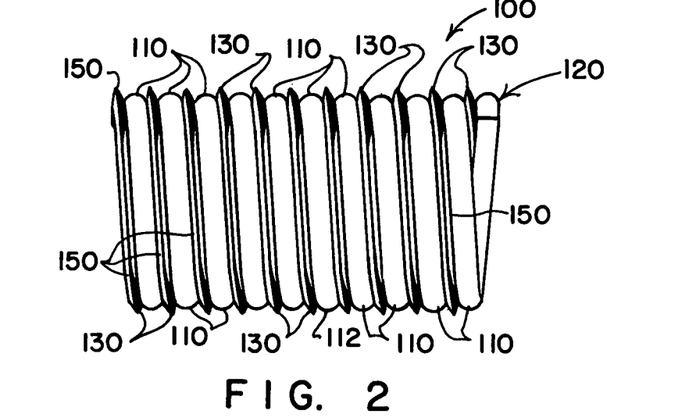
FIG. 2 is a side elevational view of the hose length, with the flexible hose in its normally fully contracted condition.
Figure 3:
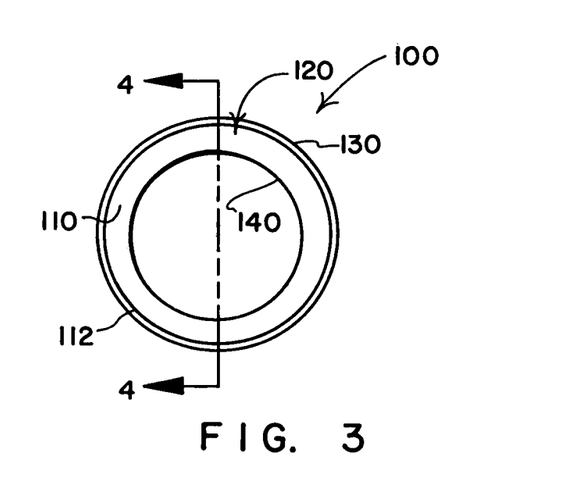
FIG. 3 is a right end view of the hose length.

Referring to FIGS. 1-3, a length of flexible, stretchable, crush resistant hose embodying features of the present invention is indicated generally by the numeral 100. The hose 100 has coils 110 of a relatively stiff plastic material that form a helix 120, and has a thin web or wall 130 of plastic material that extends between the coils 110 of the helix 120.

Although the hose 100 can undoubtedly be formed in a variety of ways, a preferred manufacturing technique employed during manufacture calls for the materials that form the coils 110 of the helix 120 and the thin web or wall 130 to be extruded, either concurrently as separate extrusions of the helical coils 110 and the thin web or wall 130 that are promptly bonded or welded together while still hot following extrusion, or as a single extrusion that forms the helical coils 110 together with an integral reach of thin web or wall 130 that also is welded or bonded promptly while still hot to form the hose 100.

What is referred to by use herein of the terms "welded," "bonded," "welding" and "bonding" is a joining together, in a heated environment or as a result of an application of heat energy (whether applied by radiation, convection, the use of laser-generated light or any other known or yet to be developed technique, or a combination thereof) of thermoplastic materials from which components of the hose 100 may be formed, including but not limited to PVC, TPU, PP, TPE, ABS and other thermoplastic materials and reasonable equivalents thereof, to form what results in or amounts to an integral assembly that typically exhibits no remaining borders between adjacent portions of the bonded or welded materials. In essence, the terms "welded" and "bonded," and the terms "welding" and "bonding" are used interchangeably, with no differences of meaning intended therebetween.

As depicted in FIGS. 1 and 2, the flexible, stretchable, crush-resistant hose 100 is in its normally fully contracted condition (also referred to herein as its "normal condition"), with the coils 110 of the helix 120 situated side-by-side relatively snugly sandwiching radially outwardly extending portions 152 (FIG. 4) of the thin plastic web or wall 130 therebetween. The hose 100 has its minimal length when it is in its normal condition as depicted in FIGS. 1 and 2, and can be stretched or extended, for example as is shown in FIG. 5, which causes the coils 110 of the helix 120 to separate, and causes the outwardly extending portions 152 of the thin web or wall 130 to flatten out or "unfold," typically in the manner depicted in FIG. 5. If, during stretching or extension, the hose 100 is caused to bend or deflect (from any of the linear or straight-line configurations that are depicted in FIGS. 1, 2, 4 and 5), the crush resistant character of the hose 100 will permit the bending or deflection to take place without significantly diminishing the inner diameter (designated by the numeral 140 in FIG. 3) of the hose 100.

The coils 110 of plastic material that form the helix 120 have a uniform cross-section that preferably features a rounded exterior surface 112 and a substantially flat interior surface 114. When the substantially flat interior surface 114 is viewed from an end of the length of hose 100, as is depicted in FIG. 3, it will be seen to take the form of a circle which defines the interior diameter 140 of the hose 100. These circles defined by all of the coils 110 are substantially the same diameter.

Figure 4:
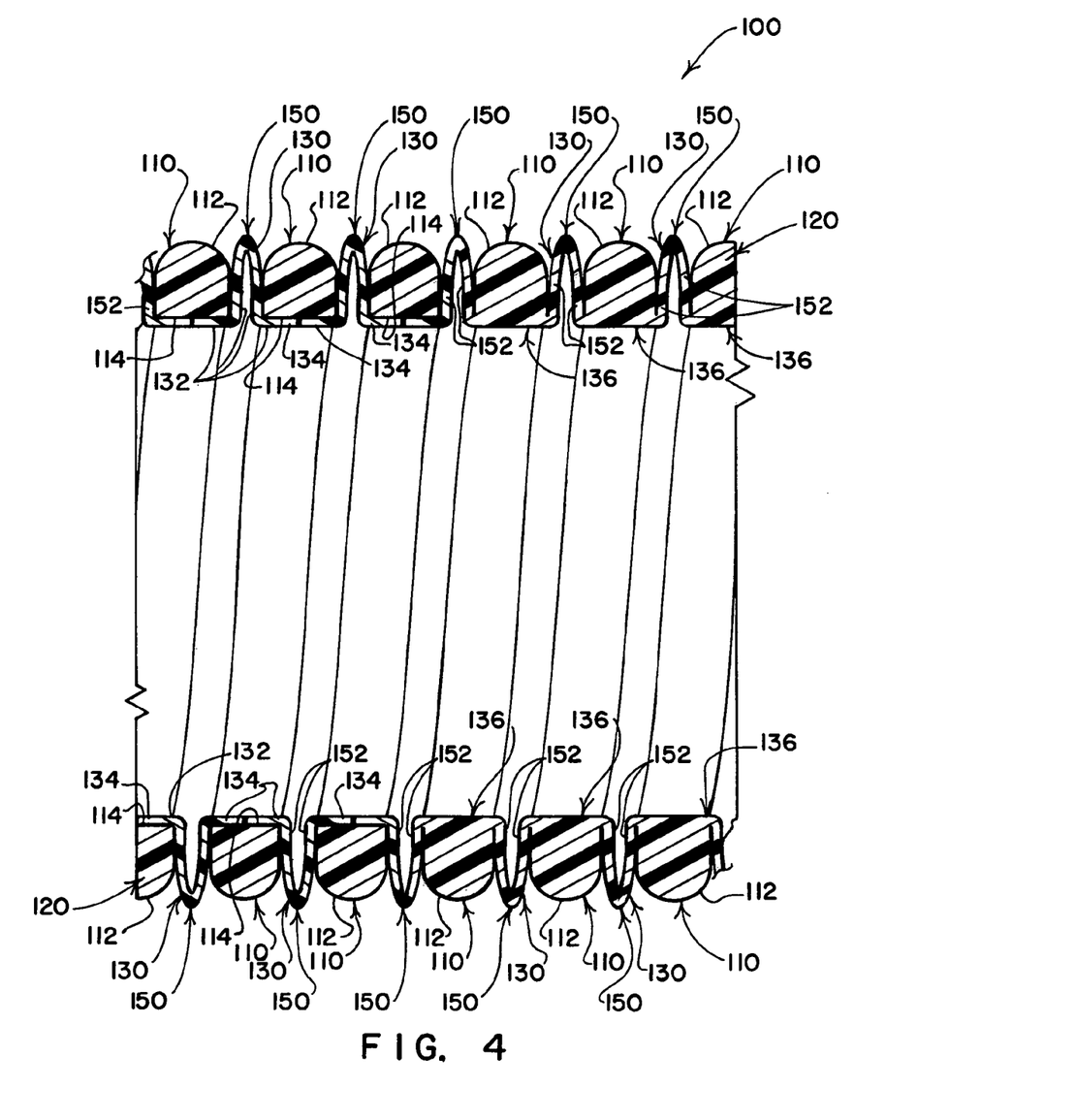
FIG. 4 is a cross-sectional view, on an enlarged scale, as seen from a plane indicated by a line 4-4 in FIG. 3, showing a portion of the length of flexible hose in a slightly less than fully contracted condition, with a left portion of the view illustrating how the thin, extruded web of plastic material has its opposite edge regions extending inside flat interior surfaces defined by the coils of the helix just prior to when the edge regions are welded by an application of heat energy to the flat interior surfaces of the coils of the helix, and with a right portion of the view showing how the cross-section changes once the welding or bonding of the web edge regions to the coils of the helix has taken place, causing the thin, extruded web and the coils of the helix to form an integral hose product.
Figure 5:
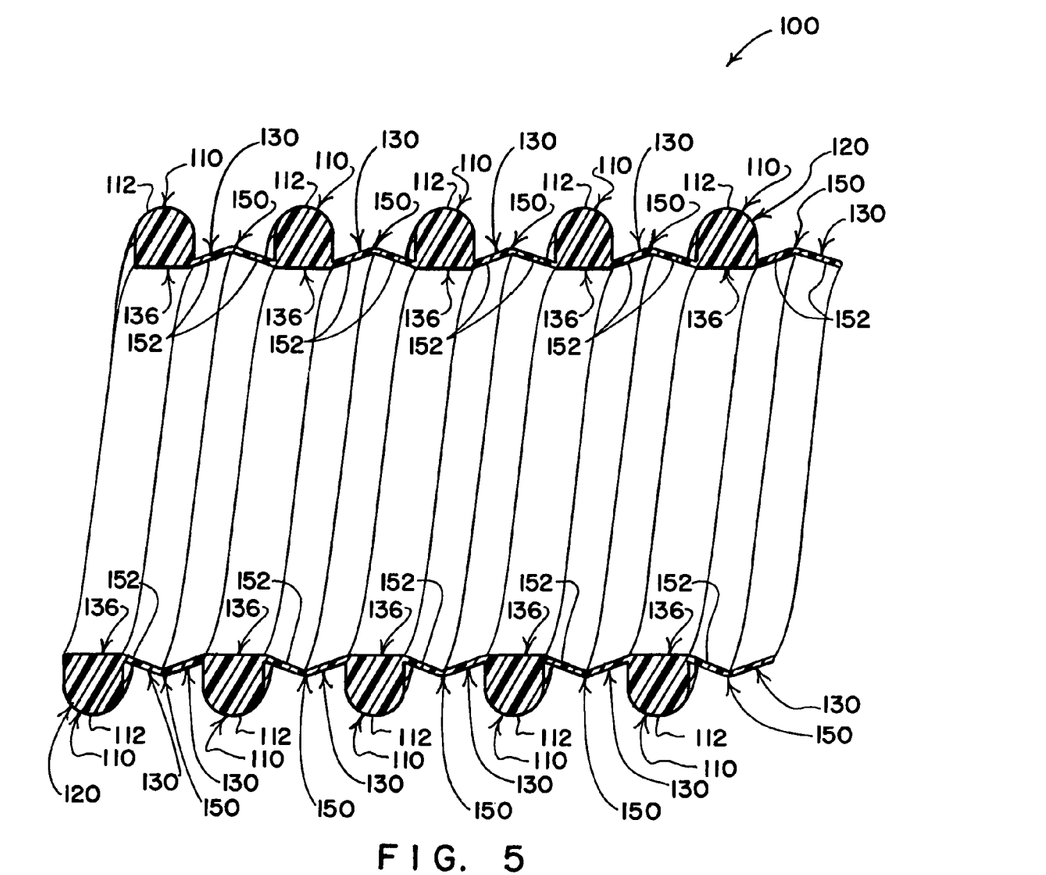
FIG. 5 is a cross-sectional view similar to FIG. 4 but showing a portion of the length of flexible hose product in an axially extended condition.

Referring to the left "half" of FIG. 4, the thin web or wall 130 that extends between adjacent pairs of the coils 110 is preferably formed by extruding a thin, flat, elongate, tape-like or band-like web of plastic material 132 that ultimately has its opposite edge regions 134 bonded or welded to the flat interior surfaces 114 of the coils 110. As is shown somewhat schematically in the left "half" of FIG. 4, the edge regions 134 of the thin wall or web 130 each preferably extend about halfway into and along the flat interior surfaces 114 of the coils 110—at which locations the edge regions 134 are welded or bonded to the flat surfaces 114 by an application of heat energy to form an integral hose 100, in a manner that is depicted in the right "half" of FIG. 4.

In essence, such boundaries as exist between the edge regions 134 and the flat interior surfaces 114 (as depicted in the left "half" of FIG. 4 at a time before welding or bonding takes place) effectively "disappear" as the thermoplastic materials forming the coils 110 and the web edge regions 134 merge and integrally bond during welding or bonding to form the integral hose product 100 that is shown in the right "half" of FIG. 4.

If identical thermoplastic materials are used to form the coils 110 of the helix 120 and the thin web or wall 130, the hose 100 that results when a proper thermoplastic welding or bonding process has been completed is a one-piece member with no discernible borders or boundaries.

If, on the other hand, different thermoplastic materials (for example a material used to form the coils 110 of the helix 120 that has a higher modulus of elasticity than does a material used to form the thin web or wall 130) are separately extruded and properly thermoplastically welded or bonded to form the hose 100, the material of the web or wall 130 may provide a contiguous, continuous and uninterrupted liner that shields the material of the coils 110 of the helix 120 from contact with gases and the like that flow through the inner diameter 140 of the hose 100—which, in certain medical applications may be of importance to prevent interactions between the material forming the coils 110 of the helix 120 and certain medications being carried by gases flowing through the hose 100.

To enhance the stretchability and flexibility of the hose 100 without diminishing its crush resistance, and to thereby avoid the problems of stiffness that are characteristic in many of the crush resistant hoses of prior proposals, the bonded or welded hose product 100 is subjected to an annealing process that modifies the orientation of the molecules of thermoplastic that forms the coils 110 of the helix 120 and the thin wall or web 130 that extends between the coils 110 of the helix 120.

When the hose 100 initially is formed, the coils 110 of the helix 120 are relatively widely spaced, and the thin web of plastic material that extends between adjacent pairs of the coils 110 takes a cylindrical shape that does not project radially outwardly at locations between the coils 110 of the helix 120. However, as the annealing process is carried out, the coils 110 of the helix 120 are moved closer and closer toward each other, which causes the web 130 situated between adjacent pairs of the coils 110 to bulge radially outwardly, creating the radially outwardly extending portions 152. As the elements of the hose 100 come to the "normal condition" depicted in FIGS. 1 and 2) wherein the coils 110 assume side-by-side positions snugly sandwiching the radially outwardly bulging web 130 therebetween, a reverse-direction crease or fold 150 (see FIGS. 4 and 5) is caused to form and set at a central location extending along the length of the tape-like or band-like web or wall 130.

As the heating and controlled cooling of the annealing process is completed with the hose 100 in its minimal-length "normal condition" (as depicted in FIGS. 1 and 2), the molecules of the material of the coils 110 and the web or wall 130 relax and take on a new orientation with a memory of the "normal condition" to which the completed hose 100 will normally return when released from the imposition of external forces (including the force of gravity). And, because stress is substantially absent from the hose 100 when the coils 110 of the hose 100 are side-by-side compressing the radially extending web or wall portions 152 therebetween (i.e., when the hose 100 is in its "normal condition" as depicted in FIGS. 1 and 2), the hose 100 begins resisting extension only when, and to the extent that, the hose 100 is stretched causing it to lengthen.

Stated in another way, the annealing process to which the hose 100 is subjected allows the hose 100 to exhibit a greater degree of flexibility and an ease of being stretched than are exhibited by conventional, non-annealed hose products, and enables the hose 100 to, in effect, provide a "strain relief" between medical delivery equipment (not shown) that typically is connected to one end region of a length of the hose 100, and a patient's facial or nasal mask (not shown) that typically is connected to an opposite end region of the same length of hose 100 in medical applications that often make use of the hose 100.

Yet another benefit of the annealed and stress-relieved hose 100 (which results from stresses that were introduced during the manufacture of the hose 100 being relieved during annealing) is that the stress-relieved hose 100 does not take a set (i.e., does not take on a configurational memory to which the hose 100 seeks to return) when deflected or bent in any one direction or orientation for a lengthy period of time.

When the hose 100 is in its normally fully contracted condition, as is depicted in FIGS. 1 and 2, the centrally located reverse-direction crease or fold 150 that is set in the thin tape-like or band-like web or wall 130 is located radially outwardly beyond the rounded exterior surfaces 112 of the coils 110 that form the helix 120 (a feature best seen in FIG. 4). The length of the radially outwardly extending portions 152 of the web 130 (that extend from the inner diameter 140 of the hose 100 to the reverse-direction creases or folds 150 that define the outer diameter of the hose 100) provides the web or wall 130 with a greater surface area to displace during flexure of the hose 100 (than typically is found in present day hoses utilized to deliver air, medicinal gases and the like in today's medical environments)—which also helps to enhance the flexibility of the hose 100.

A feature of the hose 100 is its extensibility (i.e., the ease with which the hose 100 can be stretched). The length of the radially outwardly extending portions 152 of the web 130, and the accordion-like reverse-direction crease or fold 150 that extends radially outwardly of the curved outer surfaces 112 of the coils 110 of the helix 120 gives the hose 100 an impressive ability to extend when a patient situated near one end of a reach of the hose 100 moves relative to a medical apparatus connected to an opposite end of the reach of hose 100—which is to say that the hose 100 provides a "strain relief" that minimizes the transmission of force along the length of the hose 100.

What a length of the hose 100 typically offers is an ability to stretch (in an example manner depicted in FIG. 5) to a length of at least about one and a half times the length that is exhibited by the hose when at rest in a normally fully contracted condition (as is depicted in FIGS. 1 and 2). This extensibility characteristic represents a significant improvement in comparison with such limited extensibility as may be offered by many present day crush resistant hoses that are being utilized to deliver gases in medical applications.

When the hose 100 is extended in the manner depicted in FIG. 5, the memory of the hose 100 provides a gentle spring effect that will tend to return the hose 100 to its normal fully contracted condition (i.e., its "normal condition" as depicted in FIGS. 1 and 2) when the force causing the hose to extend diminishes and is relieved. This gentle spring effect is unlike the forceful resistance to stretching or extension that often is encountered with the use of present-day crush resistant hoses in use to deliver gases in medical applications.

When the hose 100 is extended (for example, in the manner depicted in FIG. 5), the radially extending portions 152 and the reverse-direction creases or folds 150 of the web or wall 130 are pulled radially inwardly—but not in a way that diminishes the interior diameter 140 (labeled in FIG. 3) of the hose 100 that exists after the web 130 and the coils 110 of the helix 120 are bonded or welded to form the integral hose product that is depicted in the right "half" of FIG. 4 wherein the edge regions 134 shown in the left "half" of FIG. 4 (at a time prior to bonding or welding) have become integrally bonded or welded to the coils 110 of the helix 120.

In one preferred embodiment of the hose 100, the spring tension that tends to cause the hose to retract to the normal condition builds up in the hose only when the hose is stretched, and the spring tension attributable to the thermoplastic material forming the web in proportion to the spring tension attributable to the thermoplastic material forming the coils of the support spiral is at least about 25% to at least about 50%; and, in some embodiments, this ratio may be at least about 25% to as high as at least about 90%.

In one preferred embodiment of the hose 100, the helix 120 and the web 130 are formed from the same thermoplastic copolyester elastomer, also known as TPC-ET. One suitable example of a TPC-ET material well suited to form the hose 100 is sold by E.I. Dupont deNemours & Company under the registered trademark HYTREL—the torsional stiffness of which can be relieved by heating the welded hose 100 during an annealing process. The stress relieved hose 100 that results once the annealing process is completed is of continuously wound, heat welded, thermoplastic construction, and uses no solvents or glues to bond or weld the plastic helix 120 to the edge regions 134 of the thin web or wall 130 at locations along the flat inner surfaces 114 of the coils 110 of the helix 120.

Hoses 100 embodying such features as are described herein can be produced in sizes a small as 0.315 inch inside diameter, making the hose 100 ideal for medical applications where lightweight, small diameter hoses are needed.

An objective of the annealing process to which the hose 100 is subjected is to diminish torsional stiffness of the resulting hose. Torsional stiffness is defined as how much twisting force is transmitted through the hose 100 before it "breaks away" into an arc or spiral that will absorb additional twisting force when one end is held securely to a fixed point. This could also be regarded as the "twisting yield point."

For example, when a nurse moves a piece of life support equipment connected to a patient with a hose of high torsional stiffness, a great deal of the movement is transmitted through the hose to the patient interface, which creates a potential for the interface to leak or become disconnected from the patient. However, a hose with low torsional stiffness used in the same situation will "break away" into an arc or spiral thereby reducing the force that is transmitted to the patient interface, which is less likely to cause a face mask or the like to be moved from properly engaging the face of a patient.

The torsional stiffness of a hose can be determined quantitatively by measuring the amount of force required to cause a length of the hose of approximately five to ten times the internal diameter of the hose to "break away" from alignment with an axis that extends centrally through the hose, with one end of the hose under test being connected to a torque measuring device, and with the other end being turned in a direction opposite that of the wind of the helix of the hose. The annealing process to which the hose 100 is subjected typically diminishes torsional stiffness by at least about 20 percent when compared with similar hoses presently in use in medical applications.

A hose 100 embodying features of the present invention can be formed using a two step manufacturing process. A first step is to continuously wind a molten plastic (preferably a thermoplastic copolyester elastomer) profile in the shape of both the thin wall 130 and the helix 120 portions of the hose 100 around a series of spinning mandrels that are angled to allow the profile to progress forwardly off of the mandrels. The angle is controlled to insure there is a sufficient bond of the edge regions 134 of tape-like thin wall 130 to the flat inside surfaces 114 of the coils 110 of the helix 120. The angle provides the necessary pitch of helix spacing, which is typically two to five times the final dimension of the resulting hose 100 after annealing.

A second step is to anneal the hose 100. This may be achieved by compressing the hose 100 axially, and placing the hose 100 in an oven at a temperature below the melting temperature of the plastic material that forms the hose 100, for enough time 1) to relieve such stress as was introduced during the extrusion process, and 2) to cause the fold 150 to be set into the thin wall 130 of the hose 100. The hose 100 is then removed from the oven, whereafter the hose 100 is cooled and flexed to ensure that the desired degree of flexibility has been achieved.

Although a thermoplastic copolyester elastomer (TPC-ET) material such as Dupont HYTREL is a preferred material from which to form all components of the hose 100, the helix 120 and the web 130 components of the hose 100 may be formed from different thermoplastic materials, or from thermoplastic materials that differ from TPC-ET. Either or both of the helix 120 and the web 130 that connects adjacent coils 110 of the helix 120 may, for example, be formed from PVC, TPU, PP, TPE or ABS thermoplastic, or from any other commercially available thermoplastic polymers or blends thereof.

When the same TPC-ET material is used to form both the helix 120 and the web 130, the helix 120 and the web 130 can be extruded from a single die. TPC-ET is desirable for use in forming the hose 100 when the hose 100 is to be used in medical applications because the TPC-ET can be steam autoclaved to sterilize the hose 100, as is desirable in medical environments.

TPC-ET material is naturally clear or translucent in thin cross-sections, such as are employed in forming the web 130 of the hose 100, and becomes opaque in thicker sections such as are employed in forming the helix 120. Thus, even though the same TPC-ET material may be used to form the web 130 and the helix 120 of the hose 100, the resulting hose 100 will likely have the appearance of being formed from two different materials.

Alternatively, the hose 100 may be formed from two different materials in order to create a totally transparent hose, or to create a two color hose, or a clear walled hose that has a specific colored helix—which may be desirable in order to "color code" particular reaches of the hose 100 so they will be consistently used to deliver only particular gases or gaseous mixtures to patients. Colorants can, of course, be added to any of the plastic materials used to form the hose 100 to achieve practically any desired color combination.

Materials having different characteristics such as a different hardness can be used to form the web or wall 130 and the coils 110 of the helix 120, which may involve the use of two separate extruders and either a co-extrusion die, or separate dies to create the web 130 and helix 120 separately, whereafter they are welded or bonded. Likewise, materials that have different moduli of elasticity may be used to form the web or wall 130 and the coils 110 of the helix 120—with, for example, the material forming the coils 110 of the helix 120 having a higher modulus of elasticity than the material forming the web or wall 130, to enhance the crush resistance of the resulting hose 100.

Although the invention has been described in its preferred form with a certain degree of particularity, it is understood that the present disclosure of the preferred form has been made only by way of example, and that numerous changes in the details of construction and the manner of manufacture may be resorted to without departing from the spirit and scope of the invention. It is intended to protect whatever features of patentable novelty exist in the invention disclosed.

Added Disclosure of this Continuation-in-Part Application

Figure 6:
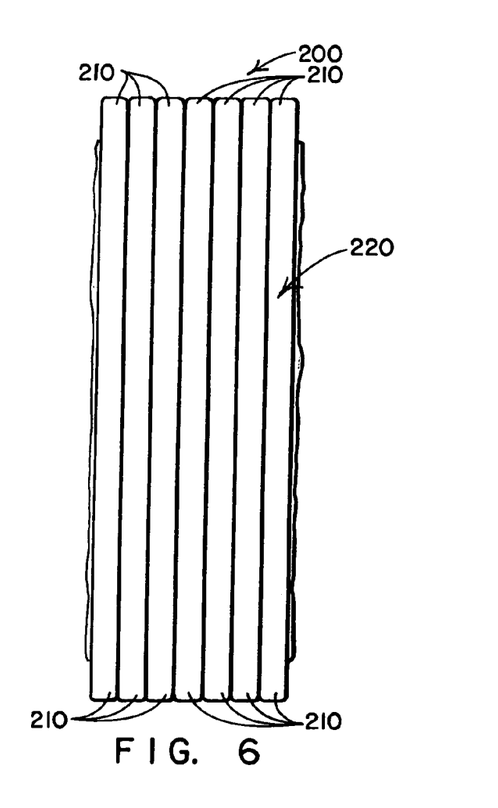
FIG. 6 is a side elevational view showing the exterior of a short length of flexible, stretchable, crush resistant hose embodying features of the present invention, with the hose shown in its normally fully contracted condition.
Figure 7:
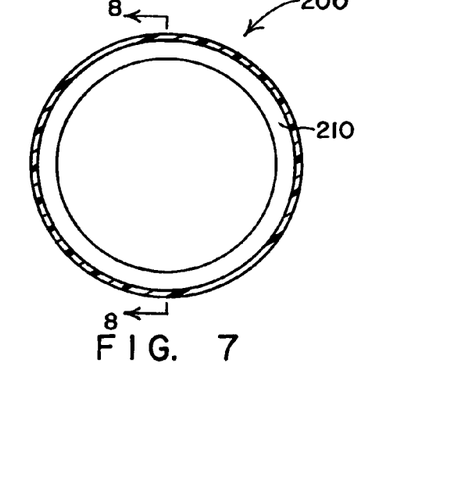
FIG. 7 is an end view, on a reduced scale, of the hose length of FIG. 6.

Referring to FIG. 6, a short segment, reach or length of a stretch hose is indicated generally by the numeral 200. The stretch hose length 200 is improved (in comparison to the hose length 100 of FIGS. 1-5) in that 1) the hose length 200 has radially inwardly extending web portions 230 (best seen in FIG. 10) that extend between and connect each adjacent pair of reinforcing coils 210 (whereas the hose length 100 has radially outwardly extending web portions 130 that extend between and connect each adjacent pair of reinforcing coils 110), and in that 2) when the hose length 200 is retracted to its normal minimum length as shown in FIGS. 6-9, the web portions 230 of the hose length 200 are sandwiched between each pair of adjacent reinforcing coils 210 and (in the embodiment depicted in FIGS. 6-10) do not extend inwardly beyond the inner diameters of the reinforcing coils 210 (whereas, when the hose length 100 is retracted to its normal minimum length, the web portions 130 of the hose length 100 that are sandwiched between each pair of adjacent reinforcing coils 110 may, and often do, extend radially outwardly beyond the outer diameters of the reinforcing coils 110 as is depicted by outermost folds 150 of the web portions 130 that as shown in FIG. 4).

The reinforcing coils 210 are portions of a helix 220 of material that provides helically extending reinforcement to the hose length 200.

A problem that arises from time to time with the previously described hose lengths 100 is that the outermost crease or fold portions 150 of the thin web portions 130 are subject to wear as the hose length 100 moves about during use, and can sometimes result in puncture or failure of the hose length 100 to maintain its fluid-tight integrity, which can permit loss of such gas as is being transmitted from place to place by the hose length 100.

Conversely, a feature of the hose length embodiment 200 depicted in FIGS. 6-10 is that the thin and somewhat delicate creases or reverse folds 250 that are located at the innermost diameters of central regions of the web portions 230 are protectively situated within the confines of the adjacent reinforcing coils 210, and are not exposed to rubbing or other engagements that can cause wear and failure of the hose length 200.

By ensuring that the folds 250 (which are defined by the radially innermost parts of the web portions 230) are located at a radial distance from a centerline of the hose 200 that is farther than are the inner diameters of the reinforcing coils 210 from the centerline, the hose 200 is assured of having an inner diameter unobstructed by the creases or reverse folds 250 of the web portions 230. This arrangement is advantageous in ensuring that radially inwardly extending web portions 230 do not obstruct a desired flow through a central portion of the hose 299 of breathing gas or the like.

Figure 10:
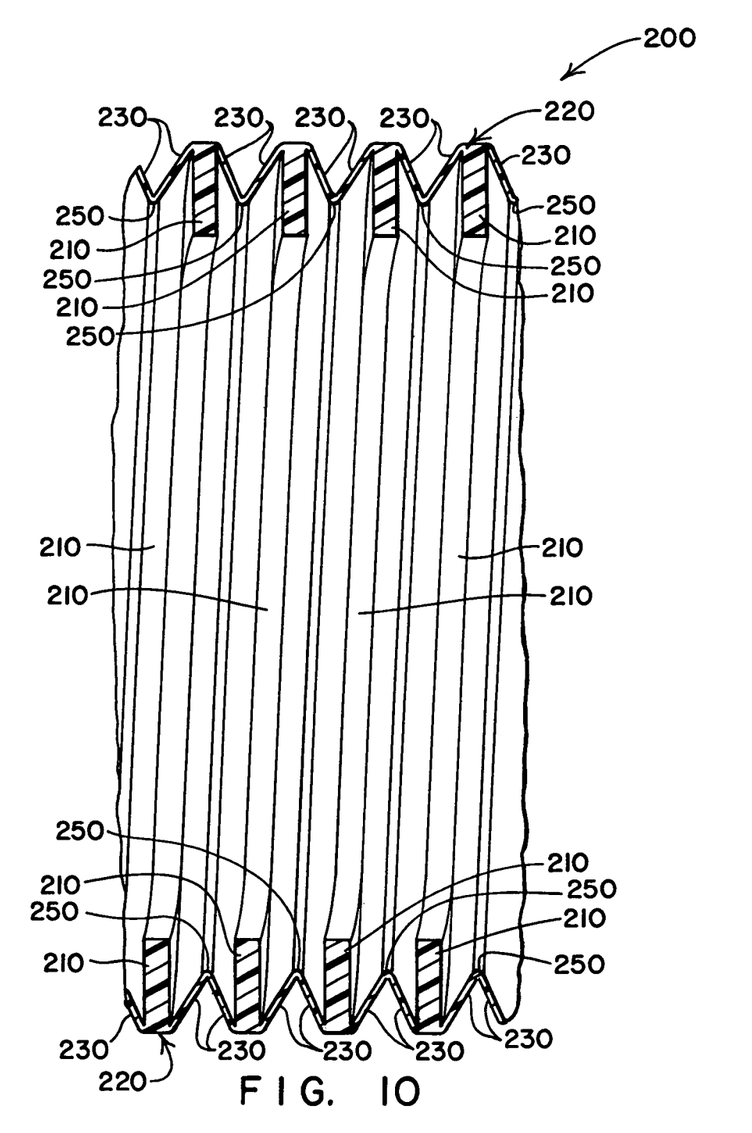

However, by forming the web portions 230 so that they are longer than the radial distance between the outer and inner diameters of the reinforcing coils 210, the hose length 200 can be provided with a capability to extend to a longer fully extended length than if the web portions 230 are kept shorter than the distances between the outer and inner diameters of the reinforcing coils 210. In some applications, this arrangement (not shown) of providing relatively lengthy web portions 230 that cause the creases or reverse folds 250 to extend radially inwardly toward a centerline of the hose 200 than the locations of the inner diameters of the reinforcing coils 210, is desirable in that it permits relatively lengthy extensions of the hose length 200 when it is necessary to stretch or elongate the hose length 200 to a greater extent than is depicted in FIG. 10.

Except for the differences explained above that have to do with the web portions 230 extending radially inwardly as opposed to the web portions 130 extending radially outwardly, such information as is presented in the specification of parent application Ser. No. 12/799,263 regarding the hose length 100 and its method of manufacture is substantially all applicable to the hose length 200 and its method of manufacture.

The hose length embodiment 200 depicted in FIGS. 6-10 has uniform sized reinforcing coils 210 that are formed by a bead or rib of thermoplastic material that has been extruded by or from a conventional extrusion apparatus (not shown) such as is commonly used in the formation of helically reinforced thermoplastic hose, as is well known to and readily understood by those who are skilled in the art.

The reinforcing coils 210 are typically formed by causing a freshly extruded bead or rib of thermoplastic material to be helically wrapped about a spinning mandrel, for example of the general type shown in the drawings of application Ser. No. 13/507,172 filed Jun. 11, 2012 by Martin E. Forrester et al entitled TAPERED HELICALLY REINFORCED HOSE AND ITS MANUFACTURE, the disclosure of which is incorporated herein by reference.

Figure 8:
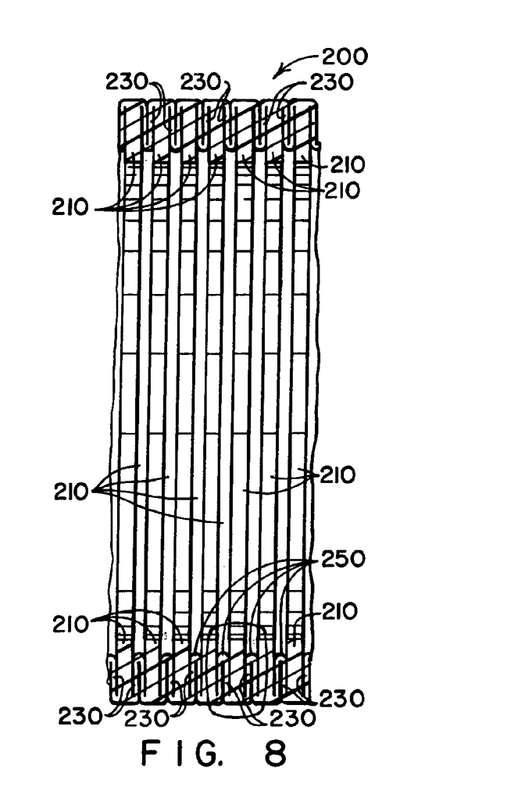
FIG. 8 is a sectional view of the hose length of FIGS. 6 and 7, as seen from a plane indicated by a line 8-8 in FIG. 7.

In the hose embodiment 200 shown in FIGS. 6-10, it will be seen that the outer and inner diameters of the reinforcing coils 210 also define outer and inner diameters of the hose length 200 when the hose 200 assumes its minimal length, as is shown in FIG. 8.

Although the reinforcing coils 110 shown in FIGS. 1-5, and the reinforcing coils 210 shown in FIGS. 6-10 hereof are depicted as being of uniform diameter and as being formed from an extruded bead of thermoplastic material that has a particular cross-section, features of the present invention can be advantageously incorporated into and utilized by hoses 100 and 200 that taper because their reinforcing coils 100, 200, respectively, are of progressively larger or progressively smaller diameters (such as are depicted in the drawings of the above-referenced application Ser. No. 13/507,172 filed Jun. 11, 2012), and/or that have various other cross-sectional configurations. The above-referenced application Ser. No. 13/507,172 filed Jun. 11, 2012 also explains how spirally reinforced hose that tapers or otherwise changes in diameter can be formed by helically wrapping extruded thermoplastic materials about a spinning mandrel.

Although the hose lengths 100, 200 can undoubtedly be formed in a variety of ways, a preferred manufacturing technique calls for the thin web or wall 130, 230, respectively, to be extruded in a tape-like form substantially concurrently with but separately from the extrusion of a bead or rib that forms the coils 110, 210, respectively.

During manufacture of the hose 200, it is preferred that the coils 210 are preferably helically wound to provide a uniformly spaced helical array on a conventional spinning mandrel (not shown), and the tape-like thin web or wall 230 is overlaid atop the helix 220 of spaced coils 210 so that opposite edge regions of the thin tape-like web 230 rest on the outermost diameters of two adjacent reinforcing coils 210, and so that a central region of the tape-like web 230 extends or bridges between each pair of adjacent coils 210, as is best seen in the hose-extended view of FIG. 10. As the positioning of the tape-like thin web 230 to overlie adjacent pairs of the coils 210 takes place, the freshly extruded thermoplastic materials that form the coils 210 and the web 230 are still hot and quite tacky, hence edge regions of the web 230 that engage outer diameter regions of the coils 210 bond or weld and become as one, thereby defining the hose 200 as a unified thermoplastic structure.

What is referred to by use herein of the terms "welded," "bonded," "welding" and "bonding" is a joining together, in a heated environment or as a result of an application of heat energy (whether applied by radiation, convection, the use of laser-generated light or any other known or yet to be developed technique, or a combination thereof) of thermoplastic materials from which components of the hose 200 may be formed, including but not limited to PVC, TPU, PP, TPE, ABS and other thermoplastic materials and reasonable equivalents thereof, to form what results in or amounts to an integral assembly that typically exhibits no remaining borders between adjacent portions of the bonded or welded materials. In essence, the terms "welded" and "bonded," and the terms "welding" and "bonding" are used interchangeably, with no differences of meaning intended therebetween.

Figure 9:
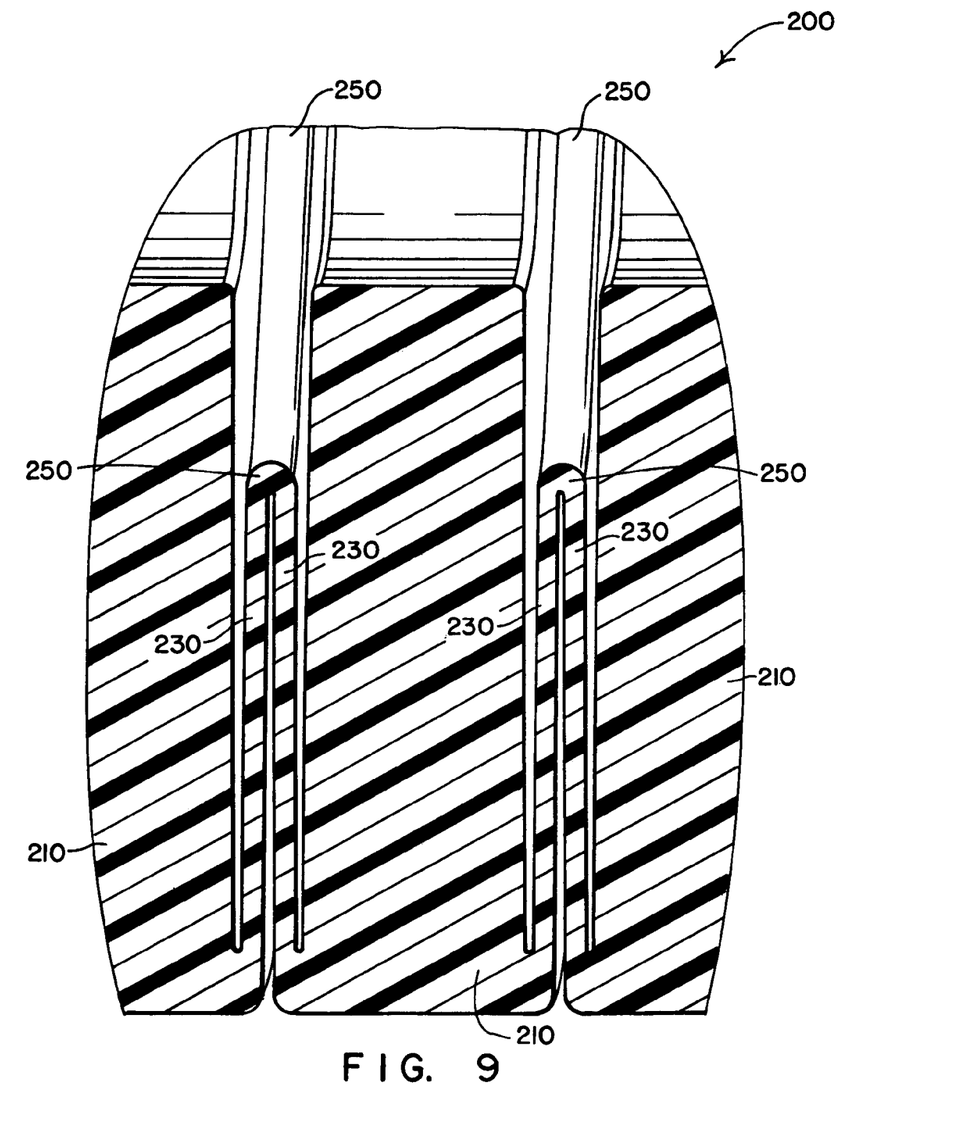
FIG. 9 is an enlargement of a selected circled portion of the sectional view of FIG. 8, showing that radially inwardly extending portions of a thin, extruded web of plastic material are snugly sandwiched between each adjacent pair of side-by-side reinforcing coils of the helix of the hose; and, FIG. 10 is a sectional view of the hose length shown in FIGS. 6-9, but with the hose length partially extended to an increased length.

As is depicted in FIGS. 6-9, the flexible, stretchable, crush-resistant hose 200 is in its normally fully contracted condition (also referred to herein as its "normal condition"), with the coils 210 of the helix 220 situated side-by-side relatively snugly sandwiching radially inwardly extending portions 230 of the thin plastic web or wall 230 therebetween, as is best shown in the enlarged sectional view provided by FIG. 9. The hose 200 has its minimal length when it is in its normal condition as depicted in FIGS. 6-9, and can be stretched or extended, for example as is shown in FIG. 10, which causes adjacent coils 210 of the helix 220 to separate, and causes the central region of the thin web or wall 230 to flatten out or "unfold," such as is partially shown in FIG. 10.

If, during stretching or extension, the hose 200 is caused to bend or deflect (from any of the linear or straight-line configurations that are depicted in FIGS. 6-10, the crush resistant character of the hose 200 will permit the bending or deflection to take place without significantly diminishing the inner diameter of the hose 200.

In preferred practice, such lengths of hose 200 as are formed by the process described above are axially compressed to their minimum length, and then are subjected to an annealing procedure which relieves stress that may have built up in the materials of the hose 200 during production. When annealing under compression is completed, stress within the materials of the hose 200 are relieved, and the resulting lengths of hose 200 always normally tend to return to their minimal length condition.

Annealing is found to enhance the stretchability and flexibility of the hose 200 without diminishing its crush resistance, and thereby serves to avoid the problems of stiffness that are characteristic in many of the crush resistant hoses of prior proposals. The bonded or welded hose product 200 is subjected to an annealing process that modifies the orientation of the molecules of thermoplastic that forms the reinforcing coils 210 of the helix 220 and the thin wall or web 230 that extends between the coils 210 of the helix 220.

As the heating and controlled cooling of the annealing process is completed with the hose 200 in its minimal-length "normal condition," the molecules of the materials of the coils 210 and the web or wall 230 relax and take on a new orientation with a memory of the "normal condition" to which the completed hose 200 will normally return when released from the imposition of external forces (including the force of gravity). And, because stress is substantially absent from the hose 200 when the coils 210 of the hose 200 are side-by-side compressing the radially extending web or wall portions 230 therebetween (i.e., when the hose 200 is in its "normal condition" as depicted in FIGS. 6-9, the hose 200 resists extension only when, and to the extent that, the hose 200 is elongated due to forceful stretching of the hose length 200.

Stated in another way, the annealing process to which the hose 200 is subjected allows the hose 200 to exhibit a greater degree of flexibility and an ease of being stretched than are exhibited by conventional, non-annealed hose products, and enables the hose 200 to, in effect, provide a "strain relief" between medical delivery equipment (not shown) that typically is connected to one end region of a length of the hose 200, and a patient's facial or nasal mask (not shown) that typically is connected to an opposite end region of the same length of hose 200 in medical applications that often make use of the hose 200.

Yet another benefit of the annealed and stress-relieved hose 200 (which results from stresses that were introduced during the manufacture of the hose 200 being relieved during annealing) is that the stress-relieved hose 200 does not take a set (i.e., does not take on a configurational memory to which the hose 200 seeks to return) when deflected or bent in any one direction or orientation for a lengthy period of time.

Another objective of the annealing process to which the hose 200 is subjected is to diminish torsional stiffness of the resulting hose. Torsional stiffness is defined as how much twisting force is transmitted through the hose 200 before it "breaks away" into an arc or spiral that will absorb additional twisting force when one end is held securely to a fixed point. This could also be regarded as the "twisting yield point," as is explained above in conjunction with the hose 100.

Although the invention has been described in its preferred form with a certain degree of particularity, it is understood that the present disclosure of the preferred form has been made only by way of example, and that numerous changes in the details of construction and the manner of manufacture may be resorted to without departing from the spirit and scope of the invention. It is intended to protect whatever features of patentable novelty exist in the invention disclosed.

What is claimed is:

1. A method of forming a flexible, stretchable, crush resistant axially extending hose, comprising the steps of providing coils entirely of thermoplastic material to form a continuous helix of substantially constant diameter, providing a thin, narrow, elongate web of thermoplastic material that extends between adjacent coils of the helix and has edge regions welded to adjacent ones of the coils to form a single continuous wall with the web having a radially inwardly extending, centrally located fold situated between adjacent ones of the coils, and enhancing the flexibility of the hose by subjecting the hose to an annealing process while axially compressing the hose so that molecules of the thermoplastic material forming the coils of the helix and the thin elongate web are relaxed such that stress is substantially absent from the hose when the coils of the helix are close together.

2. The method of claim 1 wherein the annealing process is completed while the hose is axially compressed to a minimal length normal condition wherein the coils of the helix are side-by-side snugly sandwiching radially inwardly extending portions of the web therebetween to give the resulting hose a memory of the normal condition to which the hose will tend to return when released from external force influences.

3. The method of claim 1 wherein the coils of the helix are formed to have a substantially uniform generally rectangular cross-sectional configuration that defines both the maximum outer diameter of the hose, and the minimum inner diameter of the hose when the hose is in its normal minimal length condition.

4. The method of claim 2 wherein the hose is formed such that, when the hose is in the normal condition, portions of the web that extend radially inwardly define a reverse-direction crease at a location spaced radially outwardly from the minimum inner diameter of the hose.

5. The method of claim 4 additionally including the step of utilizing the annealing process to set the reverse-direction crease.

6. The method of claim 1 additionally including the steps of forming the coils of the helix with a substantially uniform cross-section, and forming the material of the web to have a substantially uniform thickness.

7. The method of claim 1 wherein the step of providing thermoplastic material to form the helix and the step of providing thermoplastic material to form the web include providing the same thermoplastic material.

8. The method of claim 1 wherein the step of providing the thermoplastic material to form the helix includes providing thermoplastic material selected from among polyvinyl chloride (PVC), thermoplastic urethane (TPU), polypropylene (PP), thermoplastic elastomer (TPE) and acrylonitrile butadiene styrene (ABS), and the step of providing thermoplastic material to form the web includes providing thermoplastic material selected from among PVC, TPU, PP, TPE and ABS thermoplastic.

9. The method of claim 2 wherein the hose is provided with spring tension tending to cause the hose to retract to the normal condition that builds up in the hose only when the hose is stretched, with the spring tension being attributable to the thermoplastic material forming the web in proportion to the spring tension attributable to the thermoplastic material forming the coils of the support spiral being 25% to 50%.

10. The method of claim 1 wherein different thermoplastic materials are used to form the helix and the web, with the thermoplastic material forming the helix being selected to have a higher modulus of elasticity than that of the thermoplastic material forming the web.

11. The method of claim 2 wherein the thermoplastic materials selected to form the hose provide a stretch ratio of the length to which the hose can be stretched in comparison to the length of the hose in the normal condition that is at least 1.5:1.

12. The method of claim 1 wherein the thermoplastic materials selected to form the hose provide a spring constant effective when the hose is stretched that has a value of 5 N/m to 25 N/m, with these values being determined by the thickness of the web and the nature of the material selected to form the web.

13. A method of forming a flexible, stretchable, crush resistant axially extending hose, comprising helically winding newly extruded thermoplastic material to form the hose to have coils that form a continuous helix of substantially constant diameter, and a thin, narrow, elongate web that extends between adjacent coils of the helix and has edge regions welded to adjacent ones of the coils to form a single continuous wall, wherein the web has a radially inwardly extending, centrally located fold situated between adjacent ones of the coils; and annealing the hose to enhance the flexibility of the hose while the coils of the helix are compressed to cause the molecules of the thermoplastic material forming the coils and the thin thermoplastic material forming elongate web to be relaxed such that stress is substantially absent from the hose when the coils of the helix are closer together.

14. The method of claim 13 wherein the annealing process is completed while the hose is axially compressed to a minimal length condition wherein the coils of the helix are side-by-side snugly sandwiching radially inwardly extending portions of the web therebetween.

15. The method of claim 2 wherein the hose is provided with spring tension tending to cause the hose to retract to the normal condition that builds up in the hose only when the hose is stretched, with the spring tension being attributable to the thermoplastic material forming the web in proportion to the spring tension attributable to the thermoplastic material forming the coils of the support spiral being 25% to 90%.

* * * * *